US008404440B2

(12) United States Patent
Solli et al.

(10) Patent No.: US 8,404,440 B2
(45) Date of Patent: Mar. 26, 2013

(54) DEVICE FOR CARRYING OUT CELL LYSIS AND NUCLEIC ACID EXTRACTION

(75) Inventors: Lars A. Solli, Klokkarstua (NO); Anja Gulliksen, Klokkarstua (NO); Frank Karlsen, Klokkarstua (NL); Tobias Baier, Mainz (DE); Rainer Gransee, Mainz (DE); Thomas Hansen-Hagge, Mainz (DE); Klaus Stefan Drese, Mainz (DE); Liv Furuberg, Oslo (NO)

(73) Assignee: Norchip A/S, Klokkarstua (NO)

( * ) Notice: Subject to any disclaimer, the term of this patent is extended or adjusted under 35 U.S.C. 154(b) by 149 days.

(21) Appl. No.: 12/663,338

(22) PCT Filed: Jun. 9, 2008

(86) PCT No.: PCT/GB2008/001956
§ 371 (c)(1),
(2), (4) Date: Aug. 11, 2010

(87) PCT Pub. No.: WO2008/149111
PCT Pub. Date: Dec. 11, 2008

(65) Prior Publication Data

US 2010/0297754 A1 Nov. 25, 2010

(30) Foreign Application Priority Data

Jun. 7, 2007 (GB) .................................. 0710957.2

(51) Int. Cl.
*C12Q 1/68* (2006.01)
*C12M 1/00* (2006.01)
*B01D 21/00* (2006.01)

(52) U.S. Cl. ................... 435/6.1; 435/283.1; 435/287.3; 435/288.5; 422/68.1; 422/527; 422/539; 536/23.1

(58) Field of Classification Search ........................ None
See application file for complete search history.

(56) References Cited

U.S. PATENT DOCUMENTS (Continued)

FOREIGN PATENT DOCUMENTS

WO WO 02/22265 A1 3/2002
WO WO 03/060157 A2 7/2003

(Continued)

OTHER PUBLICATIONS

Boom et al., Rapid and simple method for purification of nucleic acids. J Clin Microbiol. Mar. 1990, 28(3):495-503.

(Continued)

*Primary Examiner* — Betty Forman
(74) *Attorney, Agent, or Firm* — Wolf, Greenfield & Sacks, P.C.

(57) ABSTRACT

The present invention provides an integrated lab-on-a-chip device for carrying out a nucleic acid extraction process on a fluid sample containing cells and/or particles, the device comprising: (a) a sample inlet (1) for loading of a fluid sample, (b) a lysis unit (4) for lysis of cells and/or particles present in the fluid sample, (c) a reservoir of lysis fluid (7) for the lysis unit, (d) a nucleic acid extraction unit (5) downstream of the lysis unit, and (e) reservoirs of first washing buffer and eluant fluid (8, 9, 10) for the nucleic acid extraction unit, wherein the device further comprises (f) a mixing unit (6) downstream of the nucleic acid extraction unit, and (g) a source of mixing fluid (11) for the mixing unit. The reservoirs of lysis fluid, first washing buffer and eluant fluid may be provided parallel to one anther so that they may be actuated by a single pump.

16 Claims, 7 Drawing Sheets

U.S. PATENT DOCUMENTS

| | | | | |
|---|---|---|---|---|
| 6,344,326 | B1 * | 2/2002 | Nelson et al. | 435/6.12 |
| 6,403,367 | B1 | 6/2002 | Cheng et al. | |
| 2002/0045246 | A1 * | 4/2002 | McMillan et al. | 435/306.1 |
| 2003/0138819 | A1 | 7/2003 | Gong et al. | |
| 2003/0186295 | A1 | 10/2003 | Colin et al. | |
| 2004/0151629 | A1 | 8/2004 | Pease et al. | |
| 2005/0053952 | A1 | 3/2005 | Hong et al. | |
| 2005/0142565 | A1 | 6/2005 | Samper et al. | |
| 2010/0105029 | A1 * | 4/2010 | Ririe et al. | 435/6 |

FOREIGN PATENT DOCUMENTS

| | | | |
|---|---|---|---|
| WO | WO 2004/009849 | A1 | 1/2004 |
| WO | WO 2004/039977 | A1 | 5/2004 |
| WO | WO 2005/073691 | A1 | 8/2005 |
| WO | WO 2006/121997 | A2 | 11/2006 |
| WO | WO 2008/055257 | A2 | 5/2008 |

OTHER PUBLICATIONS

Davison, The effect of hydrodynamic shear on the deoxyribonucleic acid from T(2) and T(4) bacteriophages. Proc Natl Acad Sci U S A. Nov. 1959, (11):1560-8.

Hengen, Shearing DNA for genomic library construction. Trends Biochem Sci. Jul. 1997, (7):273-4.

* cited by examiner

DEVICE FOR CARRYING OUT CELL LYSIS AND NUCLEIC ACID EXTRACTION

RELATED APPLICATIONS

This application is a national stage filing under 35 U.S.C. §371 of international application PCT/GB2008/001956, filed Jun. 9, 2008, which was published under PCT Article 21(2) in English.

The present invention relates to an integrated lab-on-a-chip diagnostic device for carrying out combined cell lysis and nucleic acid (NA) extraction. The system may be used to extract nucleic acid from a test sample containing cells and/or particles.

BACKGROUND OF THE INVENTION

The analysis of DNA and/or RNA from bacterial cells and virus particles is a key step in many areas of technology such as, for example, diagnostics, environmental monitoring, forensics and molecular biology research. In order to analyze samples containing nucleic acids, it is usually necessary to carry out two procedures. Firstly, the sample is broken down, isolated and concentrated to produce a purified nucleic acid extract. Secondly, the purified nucleic acid extract is amplified in order increase the amount of nucleic acid present to facilitate detection of the nucleic acid.

Conventionally, extraction, purification and amplification of the nucleic acid is carried out manually in a laboratory by a trained technician. This not only requires the presence of a skilled user, it also leads to a significant error rate due to user errors. In addition, this conventional extraction requires the extraction, purification and amplification to take place away from the point-of-care and, as a result, the result of the biological assay is delayed. Therefore, there is a need for providing a biological assay that reduces and simplifies user input and allows the assay to be carried out when and where the sample is actually taken, for example within the doctor's surgery, the clinic, the veterinary surgery or even in the patient's home or in the field.

Microfabricated "lab-on-a-chip" devices are an attractive option for carrying out contained biological reactions. These devices require minimal reagent handling by the user and also permit the use of small sample volumes, a significant advantage for biological reactions which require expensive reagents.

One previous approach to providing a microfabricated "lab-on-a-chip" device to extract and purify a sample comprising a nucleic acid is described in WO 2005/073691. In this document, a sample containing cells and/or particles is filtered. The filtrate (i.e. the cells and/or particles) is subject to lysis by a lysis fluid. Then, the lysed sample is passed through a nucleic acid extraction unit. The nucleic acids are extracted and remain in the extraction unit whereas the lysis fluid passes through the unit. An example of a suitable nucleic acid extraction method involves the binding of DNA to silica particles in the presence of a chaotropic agent (see Boom et al, J. Clin. Microbiol. 1990, 28, 495-503). The extracted nucleic acids are washed with one or more washing solvents, followed by extraction of the nucleic acids with an eluant. This step also serves to concentrate the nucleic acid.

WO 2005/073691 describes how a single pump may be used to actuate all fluids within its system once the sample has been syringed into the system. WO 2005/073691 then describes one way of achieving this, namely to provide the lysis fluid, washing fluids and eluant in a single channel separated by air gaps.

Once the nucleic acid has been extracted, concentrated and purified, it is then usually necessary to amplify it. While conventionally the Polymerase Chain Reaction (PCR) technique is used, a different amplification technique that may be used in some circumstances is Nucleic Acid Sequence Based Amplification (NASBA). As will be appreciated by the person skilled in the art, NASBA is different from PCR in several ways. In particular, PCR involves thermal cycling of a sample that generally produces only DNA amplification products while NASBA is an isothermal technique that is generally used to produce RNA amplification products.

A microfabricated system that is especially designed for carrying out NASBA is described in WO 02/22265. This system comprises two chambers. The first chamber heats the sample up, denatures it and facilitates the binding of primers to the denatured sample. The second chamber contains the NASBA enzymes and heats the sample isothermally to a temperature of about 41° C.

In order to carry out amplification, it is necessary to mix the nucleic acid sample with primers. These primers require the presence of a mixing fluid. This fluid may comprise one or both of DMSO and sorbitol. In WO 02/22265, it is described how this fluid is pre-loaded into the first reaction chamber and the mixing of the sample with the fluid occurs within the first reaction chamber.

SUMMARY OF THE INVENTION

The present invention provides an improved integrated device for carrying out both cell lysis and nucleic acid (preferably mRNA) extraction, which device is pre-loaded with reagents required for cell lysis and nucleic acid extraction. The device of the invention is characterised in that the various pre-loaded reagents are loaded in a manner that can be precisely controlled and can be actuated by a single pump. In particular, the use of variable-position valves in combination with a parallel set of fluid reservoirs to contain the pre-loaded reagents allows the fluids to be precisely and reliably actuated by a single pump. Additionally or alternatively, the device is characterized in that the device comprises a means for mixing the sample with a solvent after the nucleic acid sample has been extracted and purified, prior to the sample being transferred to a nucleic acid amplification unit.

Accordingly, the present invention provides an integrated lab-on-a-chip device for carrying out a nucleic acid extraction process on a fluid sample containing cells and/or particles, the device comprising:

(a) a sample inlet for loading of a fluid sample,
(b) a lysis unit for lysis of cells and/or particles present in the fluid sample,
(c) a reservoir of lysis fluid for the lysis unit,
(d) a nucleic acid extraction unit downstream of the lysis unit, and
(e) reservoirs of first washing buffer and eluant fluid for the nucleic acid extraction unit, the device further comprising:
(f) a mixing unit downstream of the nucleic acid extraction unit, and
(g) a source of mixing fluid for the mixing unit.

In a second aspect, the invention provides an integrated lab-on-a-chip device for carrying out a nucleic acid extraction process on a fluid sample containing cells and/or particles, the device comprising:

(a) a sample inlet for loading of a fluid sample,
(b) a lysis unit for lysis of cells and/or particles present in the fluid sample,
(c) a reservoir of lysis fluid for the lysis unit, (d) a nucleic acid extraction unit downstream of the lysis unit, and (e) reservoirs of first washing buffer and eluant fluid for the nucleic acid extraction unit, wherein the reservoirs of lysis fluid, first washing buffer and eluant fluid are arranged in parallel, each reservoir having an upper end and a lower end, wherein the device further comprises:

(h) an upper variable-position valve connected to the upper ends of the reservoirs of lysis fluid, first washing buffer and eluant fluid, (i) a pump connected to the upper variable-position valve, (j) a lower variable-position valve connected to the lower ends of the at least three fluid reservoirs, (k) a first actuation channel connecting the lower variable-position valve to the lysis unit, and (l) a second actuation channel connecting the lower variable-position valve to the nucleic acid extraction unit.

The features of this second aspect may be used separately from the first aspect or may be combined with the features of the first aspect.

In a third aspect, the invention provides an integrated lab-on-a-chip diagnostic system for carrying out nucleic acid extraction and a nucleic acid sequence amplification and detection process on a fluid sample containing cells and/or particles, the system comprising a nucleic acid extraction device according to the first or second aspects of the invention and a nucleic acid amplification unit.

In a fourth aspect, the invention provides a method of carrying out a nucleic acid extraction process on a fluid sample containing cells and/or particles using an integrated lab-on-a-chip device, the method comprising:

(i) providing an integrated lab-on-chip device comprising a sample inlet, a lysis unit, a nucleic acid extraction unit, a mixing unit, and reservoir of lysis fluid, first washing buffer, eluant fluid and mixing fluid, (ii) loading a sample through the sample inlet of the device, (iii) carrying out lysis on the cells and/or particles of the sample by passing lysis fluid from the lysis fluid reservoir over the cells and/or particles, (iv) passing the lysis fluid through the nucleic extraction unit to extract nucleic acids, (v) transferring first washing buffer from the first washing buffer reservoir through the nucleic acid extraction unit, (vi) transferring eluant fluid from the eluant reservoir through the nucleic acid extraction unit to produce an eluted sample from the nucleic acid extraction unit, and (vii) mixing the eluted sample with mixing fluid in the mixing unit.

The device of the first or second aspects or the system of the third aspect may be used in this method.

In a fifth aspect, the present invention provides a method of carrying out a nucleic acid extraction process on a fluid sample containing cells and/or particles using an integrated lab-on-a-chip device, the method comprising:

(i) providing an integrated lab-on-chip device comprising a sample inlet, a lysis unit, a nucleic acid extraction unit, and reservoir of lysis fluid, first washing buffer and eluant fluid, (ii) loading a sample through the sample inlet of the device, (iii) carrying out lysis on the cells and/or particles filtered of the sample by passing lysis fluid from the lysis fluid reservoir over the cells and/or particles, (iv) passing the lysis fluid through the nucleic extraction unit to extract nucleic acids, (v) transferring first washing buffer from the first washing buffer reservoir through the nucleic acid extraction unit, and (vi) transferring eluant fluid from the eluant reservoir through the nucleic acid extraction unit to produce an eluted sample from the nucleic acid extraction unit, wherein the lysis fluid, first washing buffer and eluant fluid are actuated by a single pump.

The features of this fifth aspect may be used separately from the fourth aspect or may be combined with the features of the fourth aspect. The device of the first or second aspects or the system of the third aspect may be used in this method.

BRIEF DESCRIPTION OF THE DRAWINGS

The invention is described in relation to the following drawings. These drawings are provided as examples of the invention.

DETAILED DESCRIPTION OF THE INVENTION

Figure 1:
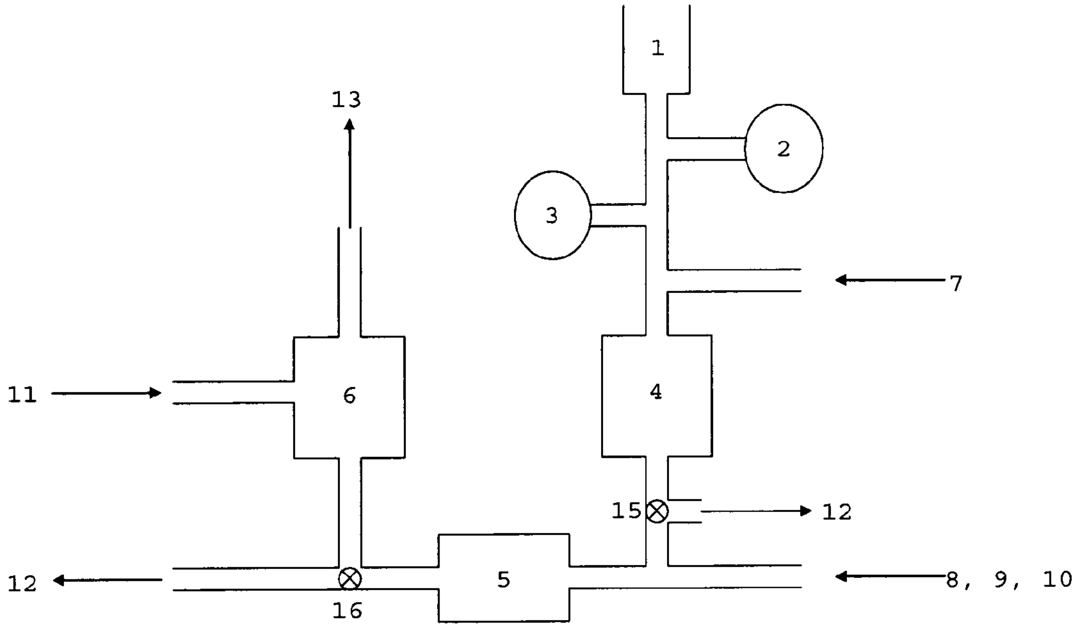
FIGS. 1 and 2 provide schematic illustrations of devices according to the invention.

The present invention provides an integrated lab-on-a-chip device for carrying out a complete sample preparation process. The device may be used in or in conjunction with, or integrally formed with, a microfabricated reaction chamber system for carrying out nucleic acid amplification and detection.

The inventors of the present invention have recognised the advantage of using the system described in WO 2005/073691 for preparing a nucleic acid sample before it is amplified. The inventors have also noted that WO 02/22265 provides a convenient microfabricated system for carrying out a nucleic acid amplification reaction, in particular NASBA. However, when trying to combine a sample preparation system such as that described in WO 2005/073691 and an amplification system such as that described in WO 02/22265, the present inventors found that sometimes the combined system showed reduced specificity and effectiveness compared to what was expected from macro-scale experiments.

The inventors found that this reduced specificity surprisingly resulted from the primers in the amplification reaction itself. In particular, WO 02/22265 suggests pre-loading all reagents for its amplification reaction into its microfabricated system prior to loading of its sample. While the inventors recognised that this approach is advantageous because it simplifies the manufacture and operation of the amplification system, the inventors found that the pre-loading of one reagent in particular can reduce the specificity of the amplification reaction. This particular reagent is the mixing fluid used in amplification to solvate the primers and mix them with the sample.

Without wishing to be bound by theory, it is thought that the mixing solvent helps to solvate primer molecules used in amplification so that the primer molecules are fully extended. If a mixing solvent is not used, the primer molecules are not fully extended and therefore the specificity of their binding is though to be reduced. The inventors have found this to be a particular issue in NASBA, where a DMSO/sorbitol mixture may be used to solvate the NASBA primers.

Therefore, the inventors looked for other ways to provide the mixing fluid. The inventors found that, by mixing the mixing fluid with the nucleic acid sample after the nucleic acid extraction and purification but before the sample is transferred to the nucleic acid amplification unit, the specificity of the binding of the primers to the sample could be increased.

Accordingly, in a first aspect, the present invention provides an integrated lab-on-a-chip device for carrying out a nucleic acid extraction process on a fluid sample containing cells and/or particles, the device comprising:

(a) a sample inlet for loading of a fluid sample,
(b) an optional filtration unit downstream of the sample inlet,
(c) a lysis unit for lysis of cells and/or particles present in the fluid sample, either integrated with the filtration unit if present or downstream of the filtration unit,
(d) a reservoir of lysis fluid for the lysis unit,
(e) a nucleic acid extraction unit downstream of the lysis unit, and
(f) reservoirs of first washing buffer and eluant fluid for the nucleic acid extraction unit, the device further comprising:

(g) a mixing unit downstream of the nucleic acid extraction unit, and
(h) a source of mixing fluid for the mixing unit.

The inventors have also recognised the advantage of using a single pump to actuate the pre-loaded reagents in the device of WO 2005/073691. In particular, the use of a single pump provides a simplified microfabricated assay. WO 2005/073691 suggests one way to design its system so it can use a single pump is to separate the lysis fluid, washing fluids and eluant in a single channel with air gaps. However, the inventors of the present invention have found that, when using this approach, the different fluids have a tendency to coalesce. This is especially a problem when using low surface energy solvents, such as alcohols (including ethanol and iso-propanol), which are typically used as washing solvents.

Therefore, in a second aspect, the present invention provides an integrated lab-on-a-chip device for carrying out a nucleic acid extraction process on a fluid sample containing cells and/or particles having a specific reagent storage unit for pre-loading and controlling the movement of its reagents. This device comprises:

(a) a sample inlet for loading of a fluid sample,
(b) an optional filtration unit downstream of the sample inlet,
(c) a lysis unit for lysis of cells and/or particles present in the fluid sample, either integrated with the filtration unit if present or downstream of the filtration unit,
(d) a reservoir of lysis fluid for the lysis unit,
(e) a nucleic acid extraction unit downstream of the lysis unit, and
(f) reservoirs of first washing buffer and eluant fluid for the nucleic acid extraction unit, wherein the reservoirs of lysis fluid, first washing buffer and eluant fluid are arranged in parallel, each reservoir having an upper end and a lower end, wherein the device further comprises:

(i) an upper variable-position valve connected to the upper ends of the reservoirs of lysis fluid, first washing buffer and eluant fluid,
(g) a pump connected to the upper variable-position valve,
(h) a lower variable-position valve connected to the lower ends of the at least three fluid reservoirs,
(j) a first actuation channel connecting the lower variable-position valve to the lysis unit, and
(k) a second actuation channel connecting the lower variable-position valve to the nucleic acid extraction unit.

The features of the second aspect may be used in the first aspect and vice versa.

As used herein, the term "downstream" means that, in use, a sample passes sequentially through the different parts of the device. While the term "downstream" includes within its scope two parts of the device being in direct fluid communication, it also includes within its scope when the two parts are separated by, for example, a valve or another part of the device. The term "integrated" means that two different parts of the device are combined into a single unit, so that, for example, the same part of the device can serve to filter the sample and act as a lysis unit. When the term "integrated" is applied to the device of the first and second aspects of the present invention combined with a nucleic acid amplification unit, it means that the two parts of the system are connected to one another so that, in use, they are in fluid communication with one another. In another aspect, the term "integrated" means that the different parts of the device are preferably formed on a common substrate. The term "connected" when applied to two parts of the device means that the two parts may be in direct fluid communication with one another (e.g. through either being joined directly together or joined through a channel) or may be separated from one another by, for example, a valve or another part of a device. Preferably, the term "connected to" means that two parts of the device are directly joined to one another.

The features of the first and second aspects will now be described in greater detail below.

The Sample Inlet

The sample inlet is designed to allow a sample to be loaded into the device. It may be suitable, for example, for injection of a sample through a syringe. The sample inlet may also be connected to a pump. In this case, the sample may be contained in a container without its own means of actuation, so that, in use, the sample is sucked into the sample inlet port by the pump.

The Filtration Unit

The device may comprise a filtration unit. This unit may either be upstream of or integrally formed with the lysis unit. The filtration unit may comprise, for example, a cross-flow filter or a hollow filter. Alternatively, the lysis unit may itself further comprise means to filter the fluid sample. Said means may comprise, for example, a cross-flow filter or a hollow filter, which may be integrated with the lysis unit.

The Lysis Unit and an Optional Nucleic Acid Fragmentation Unit

The device includes a lysis unit suitable for lysing cells present in a fluid sample (e.g. a biological or environmental fluid or a fluid sample derived therefrom) and a nucleic acid extraction unit, suitable for extracting nucleic acid (e.g. mRNA) from the contents of cells or particles lysed in the lysis unit. The lysis unit may be any lysis unit, such as that described in WO 2005/073691, the contents of which are incorporated herein in their entirety by reference. The lysis unit may have any suitable shape and configuration but will typically be in the form of a channel or chamber. The lysis unit is preferably for lysis of eukaryotic and/or prokaryotic cells and particles, e.g. virus particles, contained in the fluid sample.

If desired, the device may further comprise a nucleic acid fragmentation unit, which is downstream of the lysis unit and preferably upstream of the nucleic acid extraction unit. Alternatively, the lysis unit may itself further comprise means to fragment nucleic acid released when cells/particles in the fluid sample are lysed. Random fragmentation of DNA or RNA is often necessary as a sample pre-treatment step. Fragmentation may be achieved biochemically using restriction enzymes, or through application of a physical force to break the molecules (see, for example, P. N. Hengen, Trends in Biochem. Sci., vol. 22, pp. 273-274, 1997 and P. F. Davison, Proc. Nat. Acad. Sci. USA, vol. 45, pp. 1560-1568, 1959). DNA fragmentation by shearing usually involves passing the sample through a short constriction. In a preferred embodiment, DNA and/or RNA breaks under mechanical force when pumped through a narrow orifice, due to rapid stretching of the molecule. A pressure-driven flow can lead to a shear force, which leads to fragmentation of the nucleic acids. International patent application no. PCT/GB03/004768 describes a microfluidic device for nucleic acid fragmentation.

The lysis unit may itself further comprise means to filter the fluid sample, and optionally also means to fragment nucleic acids.

The Nucleic Acid Extraction Unit

The nucleic acid extraction unit may have any suitable shape and configuration but will typically be in the form of a channel or chamber. The nucleic acid extraction unit may be at least partially filled with beads, particles, filters or fibres of a material which binds nucleic acid (e.g. mRNA) non-specifically, e.g. silica. Alternatively or additionally, the nucleic acid extraction unit may comprise a silica filter. The nucleic acid binds to silica surfaces in the presence of chaotropic agents. The unit will typically comprise a substrate and an overlying cover, the extraction unit being defined by a recess in a surface of the substrate and the adjacent surface of the cover. The substrate is preferably formed from silicon, PDMS (poly(dimethylsiloxane)), PMMA (Polymethyl methacrylate), COC (Cyclo olefin copolymer), PE (polyethylene), PP (polypropylene), PC (polycarbonate), PL (Polylactide), PBT (Polybutylene terephthalate) and PSU (Polysulfone), including blends of two or more thereof. The preferred polymer is COC. In a particular embodiment, the nucleic acid extraction unit comprises silica bead-packed, particle filters or fibres in a channel.

Whatever the form of the nucleic acid extraction unit, the inventors have found the extraction unit to be more effective if it is treated with hydrogen peroxide before being used. This has been found to produce a sample that can be more reliably amplified. Dilution of the sample once extracted from the nucleic acid extraction unit has also been found to promote selective amplification. This can, for example, be done by having the mixing fluid comprise diluting fluid (e.g. water).

The device may further comprises means for heating the contents of the lysis unit and/or the nucleic acid extraction unit. Said mean may comprise, for example, one or more Peltier elements located in or adjacent the lysis unit and/or the nucleic acid extraction unit.

The Reagent Storage and Actuation Unit

In its most general aspect, the present invention comprises three reagent storage reservoirs, namely a lysis fluid reservoir, a first washing buffer reservoir and a eluant fluid reservoir.

In a preferred aspect, these three reservoirs are arranged in parallel. Each reservoir has two ends and these two ends are nominally given the labels upper end and lower end. The upper ends of each reservoir are connected to a first variable-position valve (nominally called the 'upper' variable-position valve) while the lower ends are connected to a second variably-position valve (nominally called the 'lower' variable-position valve). The upper variable position valve is also connected to a single pump that actuates all three reservoirs of fluid. The single pump may also actuate all other fluids pre-loaded into the device and/or the sample once loaded into the device. The lower variable position valve allows the fluids to be transferred in use to the appropriate parts of the device. In order to achieve this, the device is provided with a first actuation channel connecting the lower variable-position valve to the lysis unit and a second actuation channel further connecting the lower variable-position valve to the nucleic acid extraction unit. As a result, in use, appropriate positioning of the upper and lower variable position valve allows the single pump to actuate the lysis fluid to transfer it through the first actuation channel to the lysis unit and to actuate the first washing buffer and eluant fluid to transfer them through the second actuation channel to the nucleic acid extraction unit.

Optionally, a fourth reservoir is arranged in parallel with the other three reservoirs. This fourth reservoir is a reservoir of second washing buffer for the nucleic acid extraction unit. Again, if the two ends of this reservoir are nominally indicated as the upper end and the lower end, the upper end of this fourth reservoir is connected to the upper variable-position valve and the lower end is connected to the lower variable-position valve. The second washing buffer is actuated by the same pump that actuates the other three reservoirs. In use, the fourth washing buffer is actuated so that it is transferred through the second actuation channel to pass through the nucleic acid extraction unit.

Accordingly, each reservoir is pre-loaded with its respective reagent. The reservoir of lysis fluid is pre-loaded with lysis fluid; the reservoir of first washing buffer is pre-loaded with first washing buffer; the reservoir of eluant is pre-loaded with eluant. Optionally, the reservoir of second washing buffer is pre-loaded with second washing buffer; and the reservoir of mixing fluid is pre-loaded with mixing fluid.

By using this particular system, a reagent storage and actuation unit can be used that effectively and efficiently separates the different fluids so that they do not unintentionally mix during storage or during use. In addition, a single pump can be used to actuate all of the pre-loaded fluids. This simplifies the system and improves its reliability.

The lysis fluid can be any suitable lysis fluid/buffer capable of lysing the cells and/or particles of interest in the fluid sample. An example of a suitable lysis buffer fluid is 100 mM Tris/HCl, 8 M GuSCN (pH 6.4).

The eluant fluid can be any fluid suitable for eluting purified nucleic acids from the nucleic acid extraction unit. An example of a suitable elution buffer is 10 mM Tris/HCl, 1 mM EDTA $Na_2$ (pH 8).

The first washing solvent may be chosen from any suitable solvent, but preferably is one which can be readily evaporated, for example ethanol.

The second washing solvent may be chosen from any suitable solvent, but preferably is one which can be readily evaporated, for example isopropanol.

The mixing fluid may also be a part of this reagent storage system (see below). When used, the mixing fluid is generally a reagent which is added to purified nucleic acid eluted from the nucleic acid extraction unit for the purposes of a downstream process or reaction, for example a downstream nucleic acid amplification reaction. In one embodiment the mixing fluid may be DMSO, sorbitol or a mixture thereof. Other mixing fluids are known to the person skilled in the art (e.g. poly-alcohols, which are molecules having one or more pendant alcohol groups, such as glycerol). As noted above, these particular mixing fluids are provided in particular for NASBA.

The two variable position valves of the reagent storage and actuation system operate in concert in order to control the flow of individual reagents stored in the reagent reservoirs through the device. The first variable-position valve is denoted the upper valve and can be variably position to allow fluid communication between the pump and any of the reagent storage channels. It may also be called the pump valve. The second variable position valve is denoted the lower valve and can be variably positioned to selectively establish fluid communication between the actuation channel and each one of the reagent reservoirs, in turn. It may also be called the actuator valve. Only one of the reagent reservoirs is in fluid communication with the actuation channel at any one time, according to the selected position of the actuator valve. The lower valve enables reagent flow from each of the reagent reservoirs to be actuated using a single reagent flow actuator when the device is in use.

The use of the reagent storage and actuation system of the present invention allows the reagent flow through the device from the reagent reservoirs to the lysis unit and the nucleic acid extraction unit to be actuated according to a pre-determined protocol using a single reagent flow actuator when the device is in use.

The Mixing Unit

The device of the present invention may further comprise a separate mixing unit in order to pre-mix a sample with a mixing fluid before the sample is loaded into the first reaction chamber of an amplification unit. The inventors have found that, despite increasing the complexity of the device, this modification of the device in fact provides much more efficient and effective mixing of the sample with the mixing fluid. This can increase of the specificity of an amplification reaction carried out in the downstream amplification unit.

Accordingly, the device may further comprise a mixing unit downstream of the nucleic acid extraction unit so as to receive eluate from the extraction unit when the device is in use. The mixing unit is also in fluid communication with a reagent reservoir pre-loaded with a mixing fluid. The mixing fluid may be a fluid for promoting selective hydridization of an amplification primer to its target. Examples of such solvents include a sulphoxide and/or sorbitol. An example of a sulphoxide is DMSO The mixing unit is designed to mix eluate from the nucleic acid extraction unit (or a fluid comprising the eluate, e.g. diluted eluate) with the pre-loaded mixing fluid (e.g. DMSO/sorbitol).

The mixing unit may have any suitable shape and configuration.

In one embodiment, the reservoir of mixing fluid is stored parallel to the reservoirs of lysis fluid, first washing buffer and eluting fluid. If the two ends of this reservoir are nominally indicated as the upper end and the lower end, the upper end of the mixing fluid reservoir is connected to the upper variable-position valve and the lower end is connected to the lower variable-position valve. This is a convenient way of allowing this reservoir to be actuated by the same pump as all of the other reservoirs of fluid pre-loaded onto the device. If the mixing reagent is stored in this manner, the device further comprises a third actuation channel connecting the lower variable-position valve and the mixing unit. In use, the mixing fluid may be actuated so that it is transferred through the third actuation channel to the mixing unit. This configuration allows the mixing fluid to be stored and then provided to the mixing unit when required.

Accordingly, the mixing unit may be provided with:

(i) a third variable-position valve, (ii) first and second channels having first and second ends, wherein the first ends of the first and second channels are connected to the third variable-position valve, and the second ends of the first and second channels are co-terminus, (iii) an elongated channel having first and second ends, wherein the first end of the third channel is co-terminus with the second ends of the first and second channels.

In use, this configuration allows the sample to be eluted from the nucleic acid extraction unit and then loaded into the first channel. Mixing fluid is then loaded into the second channel. Finally, the eluted sample and solvent are pumped at the same time into the elongated channel.

In this configuration, the mixing unit may further comprise a means for measuring the positions (or plugs) of the sample eluted from the nucleic acid extraction unit in the first channel and the mixing fluid in the second channel. This allows precise control of the fluids in order to ensure efficient mixing of the sample with the mixing fluid. The measuring means is preferably an optical system comprising an optical source. In order to simplify the design of the device, the optical source can be the same optical source as that used in the turbidity measurement (see below).

Alternatively, the mixing fluid can be stored in a reservoir having both ends connected to a third variable-position valve. In this case, the mixing channel or chamber may be directly connected to the third variable-position valve so that the device comprises:

a mixing unit comprising a variable-position valve connected to the outlet of the nucleic acid extraction unit and a mixing channel connected to the variable position valve, wherein the mixing fluid reservoir has both ends directly connected to the third variable position valve. The inventors have found that this is advantageous because it simplifies the operation of the mixing unit. In particular, it means that the device can be operated with either a simplified detection system for measuring the position of the sample before being loaded into the mixing channel or chamber or without any detection system at all. This has been found to increase the reliability of the device.

In whatever embodiment, the channel or chamber in which the sample and the mixing fluid mix is typically in the form of an elongated channel, possibly containing inlays or structured side walls to promote mixing. The elongated channel may be convoluted, e.g. sinuate. In order to achieve mixing of the eluate with the downstream reagent, the two fluids are combined and flowed along the elongated channel of the mixing unit. The elongated channel provides a flow path of sufficient length to enable the two fluids to mix by simple diffusion.

It should be noted that the third variable-position valve described above may facilitate control of other parts of the device. Alternatively, a separate variable position valve may be provided to facilitate actuation of the fluids around the device. In either case, the valve may operate in concert with the first and second variable-position valves. As such, it is denoted the reagent flow path control valve. This valve's roles can be to be positioned to establish fluid communication between a selected reservoir and either the lysis unit, the nucleic acid extraction unit or (in the case of reservoir pre-loaded with mixing fluid) the mixing unit. Only one of the reagent reservoirs is in fluid communication with the lysis unit, the nucleic acid extraction unit, or mixing unit (if present) at any one time, according to the selected position of the flow path control valve.

Other Features

The device according to the present invention will typically further comprise a waste unit in fluid communication with any one or any combination of the sample inlet, the lysis unit, and the nucleic acid extraction unit. Optional valves may be present to control the flow of fluid to the waste unit. The waste unit may be microfabricated and integrated with the other components.

The device is intended to be used in conjunction with a reagent flow actuator which is a means for introducing air (or other fluid) into device. For example, the reagent flow actuator may be connected to the reagent storage system. The reagent flow actuator may form part of the device or may be a separate component used in conjunction with the device. The reagent flow actuator may comprise a pump or a syringe, or a variable volume chamber in communication with the reagent storage system.

The device may further comprise, or be used in conjunction with, means for introducing a fluid sample into the sample inlet. Said means may comprise a pump or a syringe. Alternatively, such means may comprise one or more variable volume chambers in communication with the sample inlet, wherein altering the volume of the variable volume chamber(s) effects and/or restricts flow of a fluid sample into and/or out of the inlet. The variable volume chamber typically comprises a flexible membrane overlying a hollow recess in the underlying substrate. International patent application no. PCT/GB02/005945 describes a preferred fluid transport system.

The device may further comprise a turbidity sensor. The sensor may be upstream of the filtration unit. In order to simplify the design of the device, his sensor may use the same optical source as the position sensors of the mixing system.

The device may further comprise a pressure sensor. Preferably, the pressure sensor is dead-end pressure sensor rather than an in-line pressure sensor because the inventors have found that the use of a dead-end pressure sensor prevents contamination between different samples extracted and purified on the same chip.

A System for Carrying Out Nucleic Acid Extraction, Amplification and Detection

The invention also provides an integrated lab-on-a-chip diagnostic system for carrying out nucleic acid extraction and a nucleic acid sequence amplification and detection process on a fluid sample containing cells and/or particles, the system comprising a nucleic acid extraction device according to the first or second aspects of the invention and a nucleic acid amplification unit.

Typically, the nucleic acid amplification unit will be in fluid communication the nucleic acid extraction unit, or the mixing unit if present, such that the eluate from the nucleic acid extraction unit, or a mixture thereof with the solvent, can flow directly to the nucleic acid amplification unit. An optional valve may be present to control the flow of fluid therebetween. Preferably, the nucleic acid reaction unit is microfabricated and preferably integrated with the other components.

Any conventional reaction may be carried out in the reaction unit. In a particular embodiment, the reaction will enable detection and/or quantitation of specific target nucleic acid sequence. The nucleic acid reaction unit will typically comprise a nucleic acid sequence amplification unit, which enables detection of specific sequences by a nucleic acid amplification reaction. Examples include PCR and isothermal amplification techniques such as nucleic acid sequence-based amplification (NASBA). The most preferred is real-time NASBA using molecular beacon probes for detection of the amplification products.

Accordingly, in a preferred aspect, the present invention provides an integrated lab-on-a-chip diagnostic system for carrying out a sample preparation, nucleic acid sequence amplification and detection process on a fluid sample containing cells and/or particles, more preferably real time NASBA. The general features and requirements of the NASBA reaction are well known in the art. International patent application publication no. WO 02/22265 (whose contents is incorporated by reference) describes a microfabricated reaction chamber system for carrying out NASBA which can be adapted for inclusion in the system of the invention.

The nucleic acid reaction unit may have any suitable configuration. In an embodiment the reaction unit may comprise a plurality of parallel reaction channels or chambers. In one embodiment the reaction chambers/channels may be pre-loaded with reagents required for nucleic acid amplification and/or detection, e.g. reagents required for real-time NASBA. Such reagents may include enzymes, buffer components, NTPs, primers, probes etc. Reagents may be stored in a dried state and reconstituted immediately prior to use, e.g. by addition of the fluid nucleic acid sample prepared in the sample preparation portion of the system.

In one preferred embodiment, the primers for nucleic acid amplification are pre-loaded into the amplification unit. The combination of pre-loading the primers and mixing a mixing fluid with the nucleic acid sample in the mixing unit of the present invention helps to promote the specific binding of the primers to their targets. The primers may be pre-loaded into the first chambers of a plurality of two chambers arranged in parallel. Each first chamber may be connected to a common inlet port. In this case, amplification enzymes such as NASBA enzymes are provided, preferably pre-loaded, in the second chamber. All other reagents may be provided, preferably pre-loaded, into the first chamber.

The term "pre-loading" means that reagents are added to the device prior to its end use, for example during the device's manufacture. As such, solid reagents may be deposited on the device by, for example, drying a solution of the reagent by allowing the solvent in the solution to evaporate.

The nucleic acid reaction unit may further include metering means for metering aliquots of the fluid nucleic acid sample as they are introduced into the parallel reaction chambers/channels. This metering means may take any convenient form.

In a particular embodiment, the system according to the present invention can be used for lysis of cells present in a fluid sample, extraction of mRNA, NASBA amplification of one or more specific target sequences and real-time detection of the amplification products.

Microfabrication of the System

Individual components of the device may be microfabricated. In one embodiment the lysis unit, the nucleic acid extraction unit, and the reagent reservoirs of the reagent storage and actuation system are microfabricated and integrated, i.e. formed on a common substrate.

The system or at least a master version thereof will typically be formed from or comprise a semiconductor material, although dielectric (eg glass, fused silica, quartz, polymeric materials and ceramic materials) and/or metallic materials may also be used. Examples of semiconductor materials include one or more of: Group IV elements (i.e. silicon and germanium); Group III-V compounds (eg gallium arsenide, gallium phosphide, gallium antimonide, indium phosphide, indium arsenide, aluminium arsenide and aluminium antimonide); Group II-VI compounds (eg cadmium sulphide, cadmium selenide, zinc sulphide, zinc selenide); and Group IV-VI compounds (eg lead sulphide, lead selenide, lead telluride, tin telluride). Silicon and gallium arsenide are preferred semiconductor materials. The system may be fabricated using conventional processes associated traditionally with batch production of semiconductor microelectronic devices, and in recent years, the production of semiconductor micromechanical devices. Such microfabrication technologies include, for example, epitaxial growth (eg vapour phase, liquid phase, molecular beam, metal organic chemical vapour deposition), lithography (eg photo-, electron beam-, x-ray, ion beam-), etching (eg chemical, gas phase, plasma), electrodeposition, sputtering, diffusion doping, ion implantation and micromachining. Non-crystalline materials such as glass and polymeric materials may also be used.

Examples of polymeric materials include PMMA, PDMS (poly(dimethylsiloxane)), PC (Polycarbonate), (Polymethyl methylacrylate), COC (Cyclo olefin copolymer), PE (Ppolyethylene), PP (Ppolypropylene), PL (Polylactide), PBT (Polybutylene terephthalate) and PSU (Polysulfone), including blends of two or more thereof. The preferred polymer is PDMS or COC.

The device or system will typically be integrally formed. The device or system may be microfabricated on a common substrate material, for example a semiconductor material as herein described, although a dielectric substrate material such as, for example, glass or a ceramic material could be used. The common substrate material is, however, preferably a plastic or polymeric material and suitable examples are given above. The device or system may preferably be formed by replication of, for example, a silicon master.

The advantages of using plastics instead of silicon-glass for miniaturized structures are many, at least for biological applications. One of the greatest benefits is the reduction in cost for mass production using methods like microinjection moulding, hot embossing and casting. A factor of a 100 or more is not unlikely for complex structures. The possibility to replicate structures for multilayered mould inserts gives a great flexibility of design freedom. Interconnection between the micro and macro world are in many cases easier because one got the option to combine standard parts normally used. Different approaches can be used for assembly techniques, like e.g. US-welding or solvent-welding with support of microstructures, laser welding, gluing and lamination. Other features that are profitable is surface modification. For miniaturized structures addressed for biological analysis, it is important that the surface is biocompatible. By utilizing plasma treatment and plasma polymerization a flexibility and variation of assortment can be adapted into the coating. Chemical resistance against acids and bases are much better for plastics than for silicon substrates that are easily etched away. Most detection methods within the biotechnological field involves optical measurements. The transparency of plastic is therefore a major feature compared to silicon that are not transparent. Polymer microfluidic technology is now an established yet growing field within the lab-on-a-chip market.

The microfabricated device or system as herein described is also intended to encompass nanofabricated devices.

For a silicon or semiconductor master, it is possible to define by, for example, etching or micromachining, one or more of variable volume chambers, microfluidic channels, reaction chambers and fluid interconnects in the silicon substrate with accurate microscale dimensions. A plastic replica may then be made of the silicon master. In this manner, a plastic substrate with an etched or machined microstructure may be bonded by any suitable means (for example using an adhesive or by heating) to a cover.

Method of Using the Device

The devices and system of the present invention can be used according to the fourth of fifth aspects of the present invention. These method steps are summarized below:

(i) The sample is loaded through the sample inlet, (ii) the turbidity and/or pressure of the sample are optionally measured, (iii) the sample passes optionally to a filtration unit, (iv) the fluid from the sample is optionally transferred to the waste unit, (v) lysis fluid is transferred from the lysis fluid reservoir and onto the cells and/or particles of the sample; this may be carried out by passing the lysis fluid through the first actuation channel, (vi) the lysis fluid is then passed into the nucleic acid extraction unit, (vii) the fluid remaining after being passed through the nucleic acid extraction unit is optionally transferred to the waste unit, (viii) first washing buffer is transferred from the first washing buffer reservoir through the nucleic acid extraction unit and then optionally transferred to the waste unit; this may be carried out by passing the first washing buffer from the first washing buffer reservoir through the second actuation channel, (ix) second washing buffer is optionally transferred from the second washing buffer reservoir through the nucleic acid extraction unit and then optionally transferred to the waste unit; this may be achieved by passing the first washing buffer from the first washing buffer reservoir through the second actuation channel, (x) eluant fluid is transferred from the eluant reservoir through the second actuation channel through the nucleic acid extraction unit, (xi) optionally, the eluted sample is then transferred to a mixing unit, (xii) in the mixing unit, the eluted sample is mixed with mixing fluid, (xiii) then the sample is transferred to the amplification unit.

In the amplification unit, the sample may be:

(xiv) transferred to a first chamber and heated to 60° C. or above, and then (xv) transferred to a second chamber containing NASBA enzymes and heated to about 40° C.

It is apparent from the previous description of the first, second and third aspects of the present invention that modifications, additions and deletions can be made to this sequence of steps.

Fabrication of the Device

The present invention also provides a method for the manufacture of an integrated lab-on-a-chip diagnostic system as herein described which method comprises:

A. providing a substrate having an inlet recess, a lysis unit recess, a nucleic acid extraction unit recess, a lysis fluid reservoir recess and an eluant reservoir recess in a surface thereof;

B. providing a cover; and

C. bonding the cover to the substrate to create the (a) inlet, (b) the lysis unit, (c) the nucleic acid extraction unit, (d) the lysis fluid reservoir and (e) the eluant reservoir, each being defined by the respective recess in said surface of the substrate and the adjacent surface of the cover.

The term recess as used herein is also intended to cover a variety of features including, for example, grooves, slots, holes, trenches and channels, including portions thereof.

The method may further comprise the step of introducing lysis fluid into the lysis fluid reservoir either before or after bonding the cover to the substrate.

The method may further comprise the step of introducing eluant into the eluant reservoir either before or after bonding the cover to the substrate.

The method may further comprise the step of introducing e.g. ethanol into the first washing solvent reservoir either before or after bonding the cover to the substrate.

The method may further comprise the step of introducing e.g. isopropanol into the washing solvent reservoir either before or after bonding the cover to the substrate.

The substrate may be formed from silicon, for example, and the overlying cover from glass, for example. In this case, the glass cover is preferably anodically bonded to the silicon substrate, optionally through an intermediate silicon oxide layer formed on the surface of the substrate.

The recesses in the silicon may be formed using reactive-ion etching. Other materials such as polymeric materials may also be used for the substrate and/or cover. Such materials may be fabricated using, for example, a silicon replica. Alternatively, the device may be fabricated by structuring of mould inserts by milling and electro-discharge machining (EDM), followed by injection moulding of the chip parts, followed by mechanical post-processing of the polymer parts, for example drilling, milling, deburring. This may subsequently be followed by insertion of the filter, solvent bonding, and mounting of fluidic connections.

Examples of polymeric materials include PMMA (Polymethyl methylacrylate), COC (Cyclo olefin copolymer), PDMS (poly(dimethylsiloxane)) PE (Ppolyethylene), PP (Ppolypropylene), PC (Polycarbonate), PL (Polylactide), PBT (Polybutylene terephthalate) and PSU (Polysulfone), including blends of two or more thereof. COC is preferred.

Preferably, and in particular if optical observations of the contents of the cell are required, the overlying cover is made of an optically transparent substance or material, such as glass, Pyrex or COC.

Combinations of a microfabricated component with one or more other elements such as a glass plate or a complementary microfabricated element are frequently used and intended to fall within the scope of the term microfabricated used herein.

Part or all of the substrate base may be provided with a coating of thickness typically up to 1 μm, preferably less than 0.5 μm. The coating is preferably formed from one or more of the group comprising polyethylene glycol (PEG), Bovine Serum Albumin (BSA), tweens and dextrans. Preferred dextrans are those having a molecular weight of 9,000 to 200,000, especially preferably having a molecular weight of 20,000 to 100,000, particularly 25,000 to 75,000, for example 35,000 to 65,000). Tweens (or polyoxyethylene sorbitans) may be any available from the Sigma Aldrich Company. PEGs are preferred as the coating means, either singly or in combination. By PEG is embraced pure polyethylene glycol, i.e. a formula $HO—(CH_2CH_2O)_n—H$ wherein n is an integer whereby to afford a PEG having molecular weight of from typically 200-50,000, especially PEG 1,000 to 20,000; for example 15,000 to 20,000 or chemically modified PEG wherein one or more ethylene glycol oligomers are connected by way of homobifunctional groups such as, for example, phosphate moieties or aromatic spacers. Particularly preferred are polyethylene glycols PEG having a number-average molecular weight of 15,000 to 20,000. An example of this PEG is sold by the Sigma Aldrich Company as product P2263. The above coatings applied to the surfaces of the cell/chamber, inlets, outlets, and/or channels can improve fluid flow through the system. In particular, it has been found that the sample is less likely to adhere or stick to such surfaces. PEG coatings are preferred.

For a silicon or semiconductor master, it is possible to define by, for example, etching or micromachining, one or more of variable volume chambers, microfluidic channels, reaction chambers and fluid interconnects in the silicon substrate with accurate microscale dimensions (deep reactive-ion etching (DRIE) is a preferred technique). A plastic replica may then be made of the silicon master. In this manner, a plastic substrate with an etched or machined microstructure may be bonded by any suitable means (for example using an adhesive or by heating) to a cover thereby forming the enclosed fragmentation cell(s), inlet(s), outlet(s) and connecting channel(s).

In general, it is preferable for the device to be fabricated by injection molding of a plastic, for example COC. This allows facile and convenient manufacture of the device.

The device comprises a substrate with the desired microstructure formed in its upper surface. The substrate may be silicon, for example, or a plastic substrate formed by replication of a silicon master. The substrate is bonded at its upper surface to a cover, thereby defining a series of units/cells, inlets, outlets, and/or channels. The cover may be formed from plastic or glass, for example. The cover is preferably transparent and this allows observation of the fluid. If the device is to made from silicon, it may be made by DRIE or the device may be fabricated by structuring of mould inserts by milling and electro-discharge machining (EDM), followed by injection moulding of the chip parts, followed by mechanical post-processing of the polymer parts, for example drilling, milling, deburring. This may subsequently be followed by insertion of the filter, solvent bonding, and mounting of fluidic connections.

The fluid sample may be or be derived from, for example, a biological fluid, a dairy product, an environmental fluids and/or drinking water, or a fluid sample containing cells obtained or derived from a clinical tissue sample, e.g. a biopsy or similar tissue sampling method, e.g. cervical scrapings. Non-limiting examples include blood, serum, saliva, urine, milk, drinking water, marine water and pond water. For many complicated biological samples such as, for example, blood and milk, it will be appreciated that before one can isolate and purify DNA and/or RNA from bacterial cells and virus particles in a sample, it is first necessary to separate the virus particles and bacterial cells from the other particles in sample. It will also be appreciated that it may be necessary to perform additional sample preparation steps in order to concentrate the bacterial cells and virus particles, i.e. to reduce the volume of starting material, before proceeding to break down the bacterial cell wall or virus protein coating and isolate nucleic acids. This is important when the starting material consists of a large volume, for example an aqueous solution containing relatively few bacterial cells or virus particles. This type of starting material is commonly encountered in environmental testing applications such as the routine monitoring of bacterial contamination in drinking water.

The device or system is preferably designed to cater for a sample volume of 1-100 ml.

The present invention also provides an apparatus for the analysis of biological and/or environmental samples, the apparatus comprising a system as herein described. The apparatus may be a disposable apparatus.

The present invention will now be described, by way of example, with reference to the accompanying drawings.

A typically device layout is illustrated schematically in FIG. 1. The device comprises an inlet 1 for a fluid sample, a lysis unit with integrated filter 4, a nucleic acid extraction unit 5 and a mixing unit 6. The device is provided with reservoirs of lysis fluid (7), first buffer solution (8), eluant fluid (9), optionally second buffer solution (10) and mixing fluid (11).

In use, fluid is passed into the sample inlet. It may be actively pumped into the inlet by action of, for example, a syringe. Alternatively, a pump may be provided in fluid communication with the inlet so that sample is sucked into the fluid inlet from a passive storage system. This pump may be the same as or different to the pump 27 for actuating the fluids that are pre-loaded into the device.

Optionally, the system may comprise a turbidity sensor 2 and/or a pressure sensor 3. Turbidity may also measured via optical sensor assembly 2 by measuring passing and scattered light as an indicator of glycoprotein content and cell number of the sample. Pressure may be measured by the pressure sensor 3 as an indication of filter load. In use, if the sample does not have pre-determined levels of pressure and turbidity, the sample may be rejected.

Figure 2:
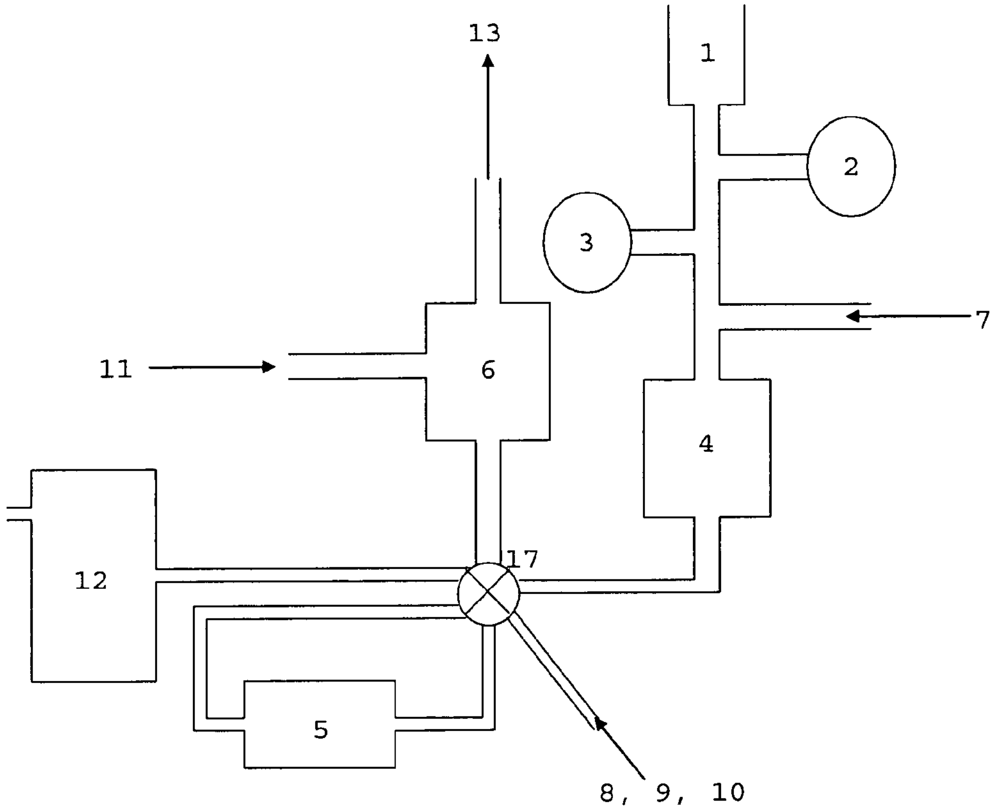

In use, fluid from the sample may be passed to the waste unit 12 once the sample has been optionally filtered. In addition, the lysis fluid and first buffer solution may be passed to a waste unit 12 when eluted from the nucleic acid extraction unit. These two outlets are shown as different outlets in FIG. 1. In this case, optional valves 15 and 16 may be used to control the flow of fluids through the fluid pathway or to the waste unit. However, more convenient approach is shown in FIG. 2. In this Figure, a single waste unit is provided. This is shown having an optional outlet so that pressure does not build up in the system. This outlet also allows gas to be released from the system during the optional air drying step of the nucleic acid purification unit. Furthermore, the flow of reagents around the chip may be controlled by one variable-position valve, referred to previously as the third variable-position valve or actuation valve. Although not shown in FIG. 2, this third variable-position valve may be provided in combination with its other functions shown in FIG. 2 or as a separate variable-position valve to provide mixing fluid 11 to the mixing unit 6.

Figure 3:
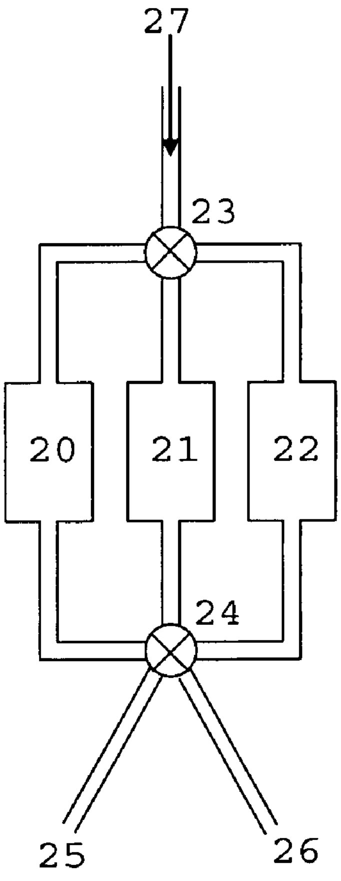
FIG. 3 shows a parallel arrangement of reagent storage reservoirs.

The reagents 7, 8, 9 and 10 may be provided in parallel reagent reservoirs. An exemplary arrangement of three parallel reservoirs is shown in FIG. 3. In this Figure, reservoirs 20, 21 and 22 are each joined at either end to variable-position valves 23 (the upper variable-position valve) and 24 (the lower variable-position valve). Reservoir 20 contains reagent 7, reservoir 21 contains reagent 8 and reservoir 22 contains reagent 9. Optionally one or two further parallel reagent reservoirs may be provided. These may contain the mixing fluid and/or the second washing buffer.

The upper variable position valve is connected to a pump 27. This pump preferably actuates all of the reagents 7, 8, 9 and, if present, 10 and 11, on the device.

The lower variable position valve is connected to first and second actuation channels 25 and 26. The first actuation channel is connected to the lysis unit so that, in use, the lysis fluid may be actuated by the pump 27 and supplied to the lysis unit through the first actuation channel. The second actuation channel is connected to the nucleic acid extraction unit so that, in use, first washing buffer and eluant fluid may be supplied to the nucleic acid extraction unit through the second actuation channel.

As will be appreciated, the concerted control of the upper and lower variable-position valves can be used to actuate all the fluids that are pre-loaded onto the device. This control can be further improved by the use of a third variable-position valve as shown in FIG. 2.

The nucleic acid extraction unit may contain silica beads, for example 0.3 mg of 15-30 μm size silica beads. Electrodes may be also provided (not shown) just below the packed bed for electrokinetic collection of the negatively charged, eluting nucleic acids.

Figure 4:
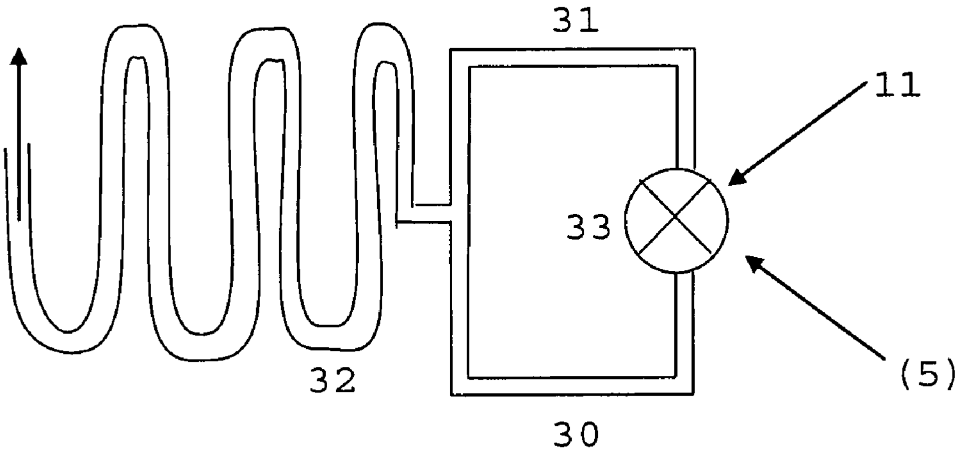
FIGS. 4 and 5 show examples of configurations of the mixing unit.
Figure 5:
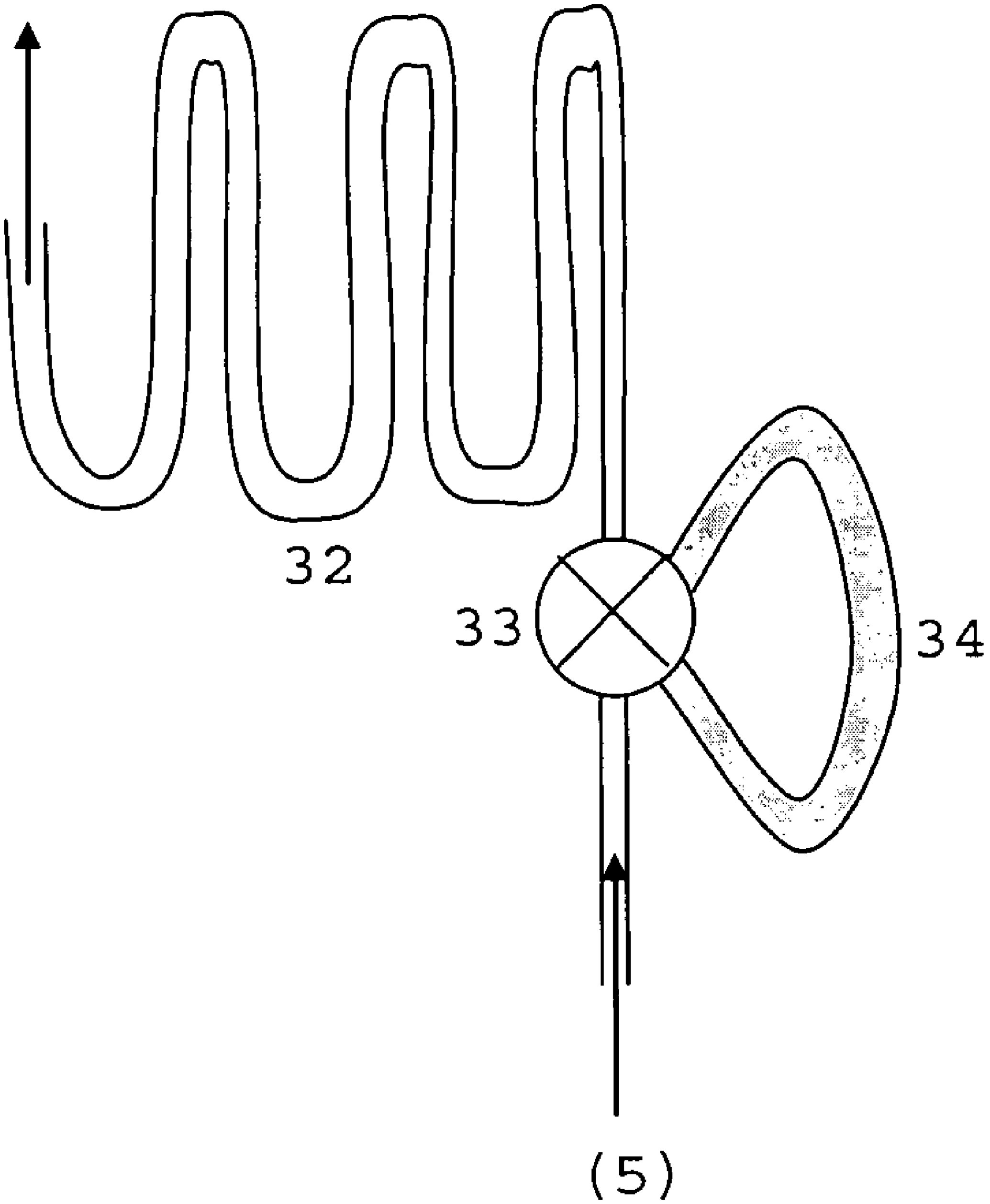

Two possible configurations for the mixing unit 6 are shown in FIGS. 4 and 5. In FIG. 4, the third variable-position valve 33 is used to position eluted sample from the nucleic acid extraction unit 5 in a first channel 30. Then, the mixing fluid 11 from the mixing fluid reservoir is loaded through the third variable-position valve 33 into a second channel 31. Once loaded, both channels are actuated. Since the channels are co-terminus at the start of the elongated mixing channel 32, the mixing fluid and eluted sample pass into the elongated mixing channel and mix. The shape of the elongated mixing channel encourages complete mixing of the sample and mixing fluid.

In FIG. 4, preferably the position of the plugs of the mixing fluid and eluted sample are measured by an optical instrument. Preferably, this optical instrument is the same optical instrument that undertakes the turbidity measurement on the sample. This is shown by the arrows in FIG. 2: a single optical detector array is provided that detects light for both the turbidity measurement (52) and the positioning of the plugs of the sample and mixing fluid in the mixing unit 55.

FIG. 5 shows an alternative configuration to FIG. 4. In particular, a third variable position valve 33 is provided directly connected to a mixing channel 32. This third variable position valve is also connected to both ends of the mixing fluid reservoir, shown as 34. The valve is also connected to the outlet of nucleic acid extraction unit 5. In use, the variable-position valve allows the mixing fluid and the sample eluted from the nucleic acid extraction unit to be mixed directly in the mixing channel without the need for a complicated optical system to measure the position of the plugs (i.e. fore-most points) of both the sample and the mixing fluid.

Figure 6:
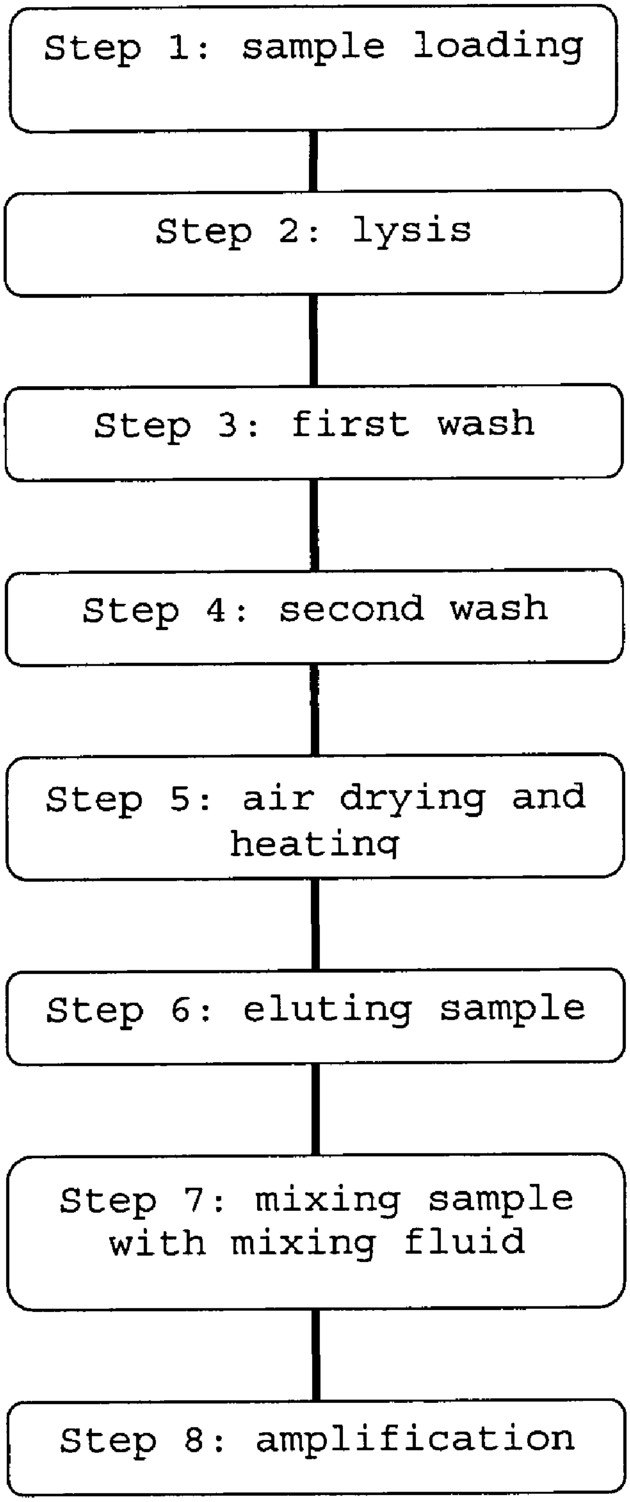
FIG. 6 is a step-by-step guide of examples of processes that may be undertaken in the device of the present invention.

Accordingly, in use, a sample loaded into the device undergoes several steps as shown in FIG. 6. Step 1 is the sample loading. 1-20 ml of fluid sample is introduced into the device via sample inlet, for example using a syringe pump, and flows through the lysis/filtration unit to waste. Cells and/or particles present in the sample are retained by the filter in the lysis unit. Pressure is measured using a pressure gauge as an indication of filter load. Turbidity is also measured via optical sensor assemble measuring passing and scattered light as an indicator of glycoprotein content and cell number of the sample.

Step 2 is the lysis. Lysis fluid is transferred from a reagent reservoir pre-loaded with lysis solution, for example through the first actuation channel. The lysis fluid is then transferred to the nucleic acid extraction unit. Cells and/or particles retained on the filter in step 1 are lysed to release their contents, the lysed sample then passes to the nucleic acid extraction unit. Nucleic acids present in the lysed sample are bound by the silica beads in the nucleic acid extraction unit and retained. Fluid exits the extraction unit and exits to the waste. If a variable-position valve is positioned connected to the outlet of the extraction unit, the valve is positioned to allow fluid flowing through the nucleic acid extraction unit to exit to the waste. In this step, all the fluids may be actuated by a single pump.

Step 3 is the first wash. The first wash solvent is transferred to the nucleic acid extraction unit, preferably through the second actuation channel. A third variable-position valve connected to the outlet of the nucleic acid extraction chamber may be positioned to allow fluid flowing through the nucleic acid extraction unit to exit to waste. All fluids may be actuated by the same single pump as in the previous step.

Step 4 is the optional second wash, e.g. with isopropanol. The details of this wash are the same as that for the first wash. Again all fluids may be actuated by the same single pump as in steps 2 to 4.

Step 5 is air drying and heating. The single pump used to actuate all fluids in steps 2 to 4 is used again to pump air through the nucleic acid extraction unit. This is achieved by, for example, leaving the fluid pathway open that allowed the second washing buffer to be pumped into the nucleic acid extraction unit. The chamber may be heated if required.

Step 6 is the elution of nucleic acid. Eluant fluid is pumped from the eluant reservoir with the same single pump used to actuate all fluids in steps 2 to 5. If present, the third variable-position valve is positioned to allow fluid flowing through the nucleic acid extraction unit to exit to the mixing unit. Nucleic acid is eluted from the nucleic acid extraction chamber and transported to the mixing unit. An optical sensor can be used to monitor arrival of eluted nucleic acid at the mixing unit.

Step 7 is the mixing. As noted previously, the exact details of this mixing step depends on the make-up of the mixing unit.

Once mixed with the mixing fluid, the sample passes to a nucleic acid amplification unit.

Figure 7:
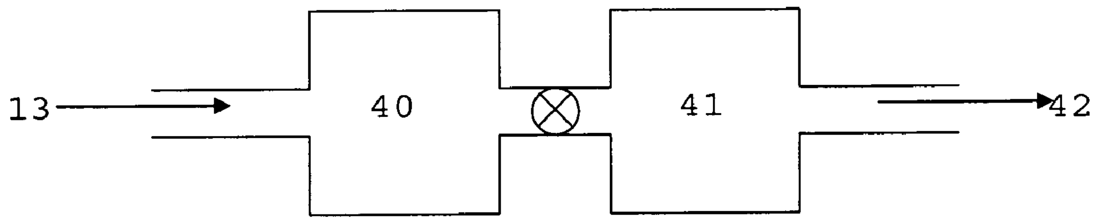
FIG. 7 is an exemplary nucleic acid amplification system.

In one embodiment, the nucleic acid amplification unit comprises a series of two chambers as illustrated in FIG. 7. In the first chamber 40, the primers for the amplification reaction are pre-loaded. They may be pre-loaded in dried form. The primers may be provided similarly pre-loaded for other configurations of nucleic acid amplification units.

In FIG. 7, if NASBA is to be carried out in the reaction chamber system, NASBA reagents are preloaded into the second chamber 41. All other reagents may also be provided preloaded in either the first or second reaction chambers or both.

Figure 8:
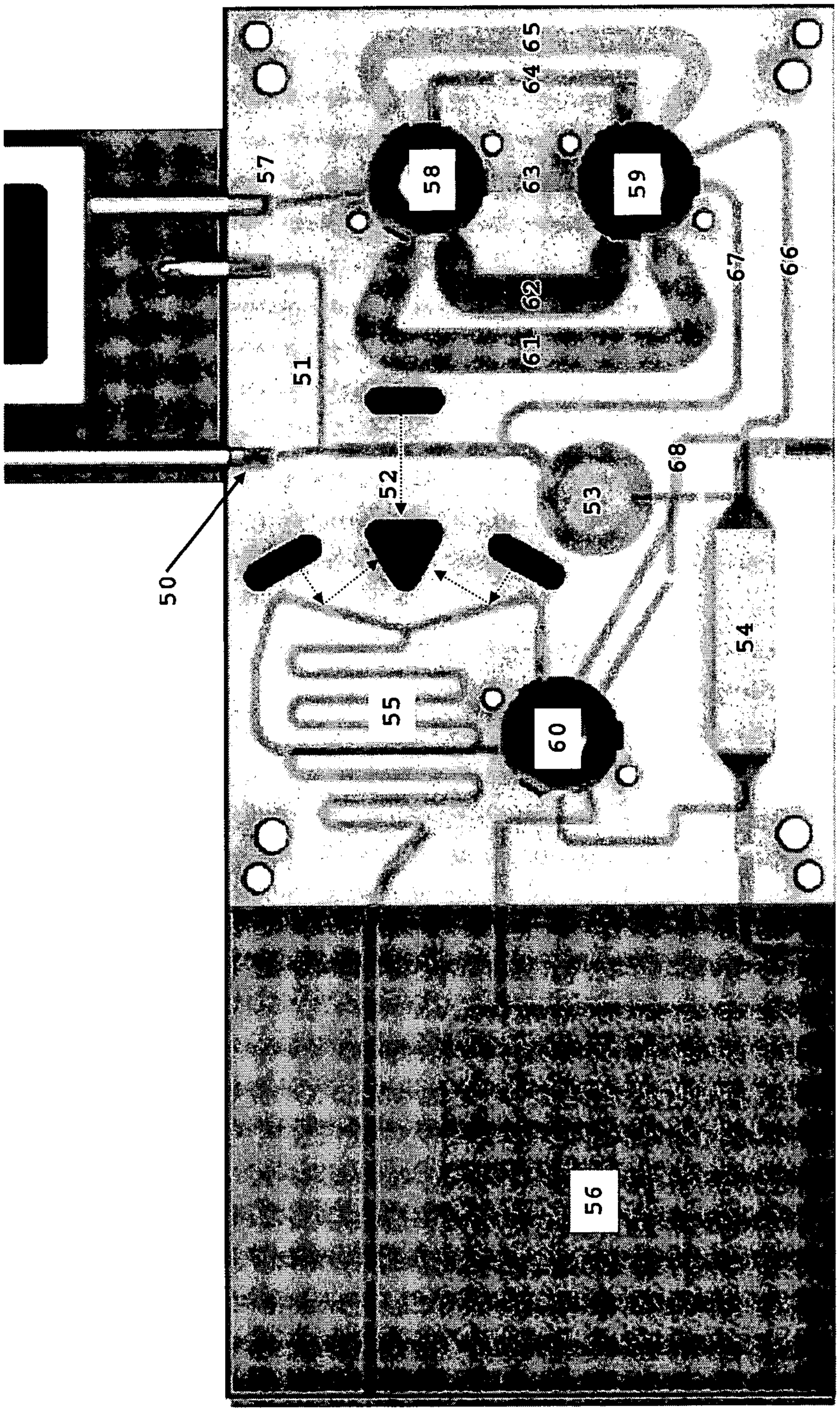
FIG. 8 shows a detailed example of the present invention.

FIG. 8 shows one possible configuration of the device of the present invention. The figure shows a sample inlet (50), a pressure sensor (51), a turbidity sensor (52) designed so that it can also be used to measure the position of the fluid in the mixing unit (55), an integrated filtration and lysis unit (53), a nucleic acid extraction unit (54), a waste unit (56), a pump (57) for actuating all fluids on the device, upper and lower variable position valves (58 and 59), a third variable position valve for both position the sample and mixing fluid in the mixing unit and for controlling the flow of fluids around the device and to the waste unit (56), reagent storage reservoirs (61, 62, 63, 64 and 65), and specific actuation channels connecting the lower variable position valve to the lysis unit, nucleic acid extraction unit and mixing unit (66, 67 and 68). A channel is seen leaving the elongated channel of the mixing unit (55), which connects to a nucleic acid amplification unit (not shown).

Figure 9:
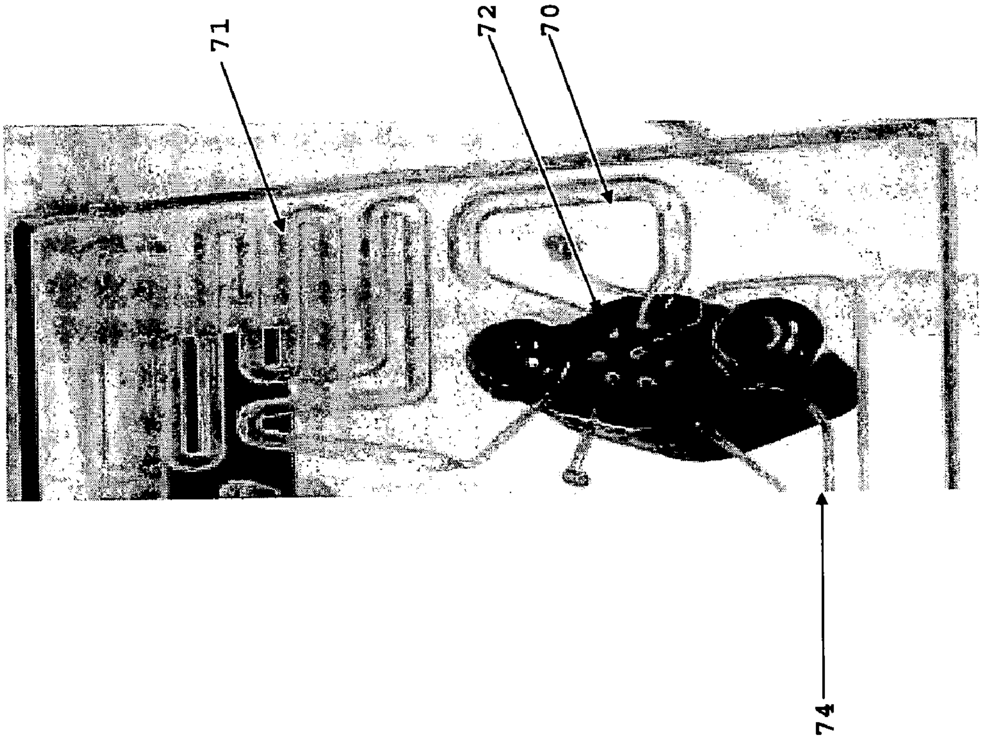
FIG. 9 shows a detailed example of a mixing unit of the present invention.

FIG. 9 shows an alternative configuration of the mixing unit. A variable-position valve (72) is used to control a mixing fluid reservoir (70). The valve is connected to a mixing channel (71). Sample is provided from the nucleic acid extraction unit through an actuation channel (74).

Accordingly, the device of the present invention can be used on millilitre sample volumes for routine diagnostics. This has been demonstrated by the present inventors on samples containing between 50 and 50000 cells. In particular, primers for HPV16 were provided in the nucleic acid amplification unit and NASBA was used to amplify the RNA extracted from cells. The above protocols were followed. In particular, 3 ml of sample was loaded into the sample inlet. The system was fabricated from COC. The silica in the nucleic acid extraction unit was pre-treated for 24 hours with 3% hydrogen peroxide. A "Genomed A" silica filter was used.

Once the sample was loaded, 120 μl of 'Biomerieux Buffer pH 7.5' was used as the lysis fluid. Then, 230 μl of 75% ethanol in water was used as the first washing buffer. The second washing buffer consisted of 100% ethanal. The nucleic acid extraction unit was dried with 7 times 4 ml air supplied at 1.5 ml/minute, the 1 times 2 ml air supplied at 1.5 ml/minute. Drying of the nucleic acid extraction unit then took place at 60° C. for 20 minutes. NASBA was then performed on the sample using primers for HPV16. A positive result was observed for the sample.

The invention claimed is:

1. An integrated lab-on-a-chip device for carrying out a nucleic acid extraction process on a fluid sample containing cells and/or particles, the device comprising:

(a) a sample inlet for loading of a fluid sample,
(b) a lysis unit for lysis of cells and/or particles present in the fluid sample,
(c) a reservoir of lysis fluid for the lysis unit,
(d) a nucleic acid extraction unit downstream of the lysis unit,
(e) reservoirs of first washing buffer and eluant fluid for the nucleic acid extraction unit, wherein the reservoirs of lysis fluid, first washing buffer and eluant fluid are arranged in parallel, each reservoir having an upper end and a lower end, (f) a mixing unit downstream of the nucleic acid extraction unit,
(g) a reservoir of mixing fluid for the mixing unit configured so that, in use, the mixing fluid is mixed in the mixing unit with a sample eluted from the nucleic acid extraction unit,
(h) a waste unit in fluid communication with the nucleic acid extraction unit,
(i) an upper variable-position valve connected to the upper ends of the reservoirs of lysis fluid, first washing buffer and eluant fluid,
(j) a pump in fluid communication with the upper variable-position valve,
(k) a lower variable-position valve connected to the lower ends of the at least three fluid reservoirs,
(l) a first actuation channel connecting the lower variable-position valve to the lysis unit,
(m) a second actuation channel connecting the lower variable-position valve to the nucleic acid extraction unit, and
(n) a third variable position valve connected to an outlet of the nucleic acid extraction unit and positioned to allow, in use, fluid flowing through the nucleic acid extraction unit to exit to the waste unit or the mixing unit, wherein the upper variable-position valve, lower variable-position valve and third variable position valve operate in concert and the lysis fluid, first washing buffer, eluant fluid and mixing fluid may be actuated by the pump in fluid communication with the upper variable-position valve.

2. The integrated lab-on-a-chip device of claim 1, further comprising:

(o) a filtration unit that is either upstream of the lysis unit or integrally formed with the lysis unit.

3. The device of claim 1 further comprising:

(p) a reservoir of second washing buffer for the nucleic acid extraction unit arranged in parallel with the reservoirs of lysis fluid, first washing buffer and eluant fluid, wherein the reservoir of second washing buffer has an upper end and a lower end, the upper end of the reservoir being connected to the upper variable-position valve and the lower end of the reservoir being connected to the lower variable-position valve, and wherein the second washing buffer is actuated by the pump (j).

4. The device of claim 1, wherein the mixing fluid comprises DMSO, sorbitol or a mixture thereof.

5. The device of claim 1, wherein the reservoir of mixing fluid is arranged parallel to the reservoirs of lysis fluid, first washing buffer and eluant fluid and has an upper end and a lower end, wherein the upper end is connected to the upper variable-position valve and the lower end is connected to the lower variable-position valve.

6. The device of claim 5, wherein the device further comprises a third actuation channel connecting the lower variable-position valve with the mixing unit.

7. The device of claim 1, wherein the mixing unit comprises:

(i) the third variable-position valve downstream of the nucleic acid extraction unit and connected to the reservoir of mixing fluid, and (ii) a mixing channel downstream of the third variable-position valve.

8. The device of claim 1, wherein the device further comprises a turbidity sensor positioned to determine the turbidity of a fluid sample loaded via the sample inlet.

9. The device of claim 1, wherein the device further comprises a pressure sensor positioned to determine the pressure of a fluid sample loaded via the sample inlet.

10. The device of claim 1, wherein the device further comprises:

(q) a waste unit, wherein the waste unit is in fluid communication with the lysis unit and/or the nucleic acid extraction unit.

11. The device of claim 1, wherein the device further comprises means for heating the contents of the lysis unit and/or the nucleic acid extraction unit.

12. The device of claim 11, wherein the means for heating comprises one or more Peltier elements located in or adjacent the lysis unit and/or the nucleic acid extraction unit.

13. An integrated lab-on-a-chip diagnostic system for carrying out nucleic acid extraction and a nucleic acid sequence amplification and detection process on a fluid sample containing cells and/or particles, the system comprising:

a nucleic acid extraction device according to claim 1, and a nucleic acid reaction unit.

14. A system as claimed in claim 13 wherein the nucleic acid extraction device and the nucleic acid reaction unit are integrally formed.

15. A method of carrying out a nucleic acid extraction process on a fluid sample containing cells and/or particles using an integrated lab-on-a-chip device, the method comprising:

(i) providing the integrated lab-on-chip device of claim 1 comprising a sample inlet, a lysis unit, a nucleic acid extraction unit, a mixing unit, and reservoir of lysis fluid, first washing buffer, eluant fluid and mixing fluid, (ii) loading a sample through the sample inlet of the device, (iii) carrying out lysis on the cells and/or particles of the sample by passing lysis fluid from the lysis fluid reservoir over the cells and/or particles, (iv) passing the lysis fluid through the nucleic extraction unit to extract nucleic acids, (v) transferring first washing buffer from the first washing buffer reservoir through the nucleic acid extraction unit, (vi) transferring eluant fluid from the eluant reservoir through the nucleic acid extraction unit to produce an eluted sample from the nucleic acid extraction unit, and (vii) mixing the eluted sample with mixing solvent in the mixing unit.

16. A method of carrying out a nucleic acid extraction process on a fluid sample containing cells and/or particles using an integrated lab-on-a-chip device, the method comprising:

(i) providing the integrated lab-on-chip device of claim 1 comprising a sample inlet, a lysis unit, a nucleic acid extraction unit, a mixing unit, and reservoir of lysis fluid, first washing buffer, eluant fluid and mixing fluid, (ii) loading a sample through the sample inlet of the device, (iii) carrying out lysis on the cells and/or particles of the sample by passing lysis fluid from the lysis fluid reservoir over the cells and/or particles, (iv) passing the lysis fluid through the nucleic extraction unit to extract nucleic acids, (v) transferring first washing buffer from the first washing buffer reservoir through the nucleic acid extraction unit, and (vi) transferring eluant fluid from the eluant reservoir through the nucleic acid extraction unit to produce an eluted sample from the nucleic acid extraction unit, wherein the lysis fluid, first washing buffer and eluant fluid are actuated by a single pump.

* * * * *

UNITED STATES PATENT AND TRADEMARK OFFICE

CERTIFICATE OF CORRECTION

PATENT NO. : 8,404,440 B2
APPLICATION NO. : 12/663338
DATED : March 26, 2013
INVENTOR(S) : Solli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 395 days.

Signed and Sealed this
First Day of September, 2015

Michelle K. Lee

Michelle K. Lee
*Director of the United States Patent and Trademark Office*